United States Patent
Coop et al.

(10) Patent No.: US 12,396,988 B2
(45) Date of Patent: Aug. 26, 2025

(54) METHODS OF USING MUSCARINIC ANTAGONISTS IN THE TREATMENT OF DEPRESSION

(71) Applicants: Andrew Coop, Columbia, MD (US); Chad R. Johnson, Baltimore, MD (US); Jack Bergman, Cambridge, MA (US); Brian D. Kangas, Boston, MA (US); James H. Woods, San Antonio, TX (US); Emily M. Jutkiewicz, Dexter, MI (US); Gail Winger, Ann Arbor, MI (US)

(72) Inventors: Andrew Coop, Columbia, MD (US); Chad R. Johnson, Baltimore, MD (US); Jack Bergman, Cambridge, MA (US); Brian D. Kangas, Boston, MA (US); James H. Woods, San Antonio, TX (US); Emily M. Jutkiewicz, Dexter, MI (US); Gail Winger, Ann Arbor, MI (US)

(73) Assignees: BOARD OF REGENTS, THE UNIVERSITY OF TEXAS SYSTEM, Austin, TX (US); UNIVERSITY OF MARYLAND, BALTIMORE, Baltimore, MD (US); THE MCLEAN HOSPITAL CORPORATION, Belmont, MA (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 885 days.

(21) Appl. No.: 17/600,347

(22) PCT Filed: Apr. 6, 2020

(86) PCT No.: PCT/US2020/026820
§ 371 (c)(1),
(2) Date: Sep. 30, 2021

(87) PCT Pub. No.: WO2020/206410
PCT Pub. Date: Oct. 8, 2020

(65) Prior Publication Data
US 2022/0152005 A1 May 19, 2022

Related U.S. Application Data

(60) Provisional application No. 62/829,178, filed on Apr. 4, 2019.

(51) Int. Cl.
*A61K 31/4406* (2006.01)
*A61K 31/439* (2006.01)
(Continued)

(52) U.S. Cl.
CPC ........ *A61K 31/4406* (2013.01); *A61K 31/439* (2013.01); *A61K 45/06* (2013.01); *A61P 25/24* (2018.01)

(58) Field of Classification Search
None
See application file for complete search history.

(56) References Cited

U.S. PATENT DOCUMENTS

| 4,837,241 A * | 6/1989 | Jensen ................. C07D 413/04 |
| | | 546/209 |
| 8,859,585 B2 * | 10/2014 | Furey ..................... A61P 25/22 |
| | | 514/304 |

(Continued)

FOREIGN PATENT DOCUMENTS

| EP | 0 259 621 | 11/1992 | |
| WO | WO-9613261 A1 * | 5/1996 | ............. A61K 31/40 |
| WO | WO-9720561 A1 * | 6/1997 | ......... A61K 31/4155 |

OTHER PUBLICATIONS

Sauerberg, Journal of Medicinal Chemistry 1991 34 (2), 687-692 (Year: 1991).*

(Continued)

*Primary Examiner* — Jeffrey S Lundgren
*Assistant Examiner* — Anthony Joseph Seitz
(74) *Attorney, Agent, or Firm* — Wenderoth Lind & Ponack LLP (57) ABSTRACT

Muscarinic antagonist are provided that are used in the treatment of depression in a subject, such as humans. The muscarinic antagonist of the invention can relieve depression without effecting cognitive functions in the treated subject.

18 Claims, 3 Drawing Sheets

(51) Int. Cl.
    *A61K 45/06*    (2006.01)
    *A61P 25/24*    (2006.01)

(56) References Cited

U.S. PATENT DOCUMENTS

2011/0195952 A1    8/2011    Seed et al.
2018/0155302 A1    6/2018    Nirogi et al.

OTHER PUBLICATIONS

Carruthers et al, The muscarinic system, cognition and schizophrenia, Neuroscience & Biobehavioral Reviews, vol. 55, 2015, pp. 393-402 (Year: 2015).*
Baker et al., J. Chem. Soc., Chem. Commun., 1992, 817-819 (Year: 1992).*
International Search Report issued Jun. 12, 2020 in International (PCT) Application No. PCT/US20/026820.

* cited by examiner

METHODS OF USING MUSCARINIC ANTAGONISTS IN THE TREATMENT OF DEPRESSION

STATEMENT OF FEDERALLY SPONSORED RESEARCH AND DEVELOPMENT

This invention was made with government support under Grant No. MH107499 awarded by the National Institutes of Health. The government has certain rights in the invention.

TECHNICAL FIELD

The invention relates generally to the field of medicine and an improved antidepressant medication. In particular, the invention relates to muscarinic antagonists that can relieve depression without disrupting cognitive effects in a treated subject, and the use of such antagonists in methods of treating depression in a subject.

BACKGROUND OF INVENTION

Major depression is a widespread psychiatric disorder demonstrating severe symptoms in how a person feels, thinks and handles daily activities. Furthermore, it is linked to diminished quality of life, medical morbidity, and mortality. Depression has a lifetime prevalence of 16% in the United States and appears to be caused by a combination of genetic, environmental, and psychological factors. To date, there are many pharmacological treatments for depression. Most of these are aimed at modifying the neurotransmission of the serotonergic or noradrenergic biochemical pathways. In addition, only one third of depressed patients who are treated with a single antidepressant achieve remission after three months. Between 2-7% of adults with this disorder die by suicide. While counseling and antidepressant medication can be effective treatments, current selective serotonin re-uptake inhibitors (SSRIs) take weeks before therapeutic effects are observed. In addition, only one third of patients who are treated initially with an SSRI achieve complete remission. The currently approved therapies require a four to six week period of chronic administration before a therapeutic effect is achieved. This delay period of action is not well understood and presents a significant challenge for medical professionals in the management of major depression. Also, the current anti-depression medications possess significant problems, including a delayed onset of action and different therapeutic effects in different patients. As a result, fully efficacious and faster-onset antidepressant drugs are urgently needed.

Mechanisms of anti-depressants have been a major focus of both past and current research in hopes of developing more effective and faster acting drugs. Related to this, clinical data (and repeat trial data in 2010, nihm.nih.gov) showed that oral and intravenous treatment with the muscarinic cholinergic treatment antagonist scopolamine had rapid anti-depressant effects in humans. This raised the interesting possibility that targeting the muscarinic cholinergic pathway could yield novel and effective anti-depressants. While side effects were not prominent in this trial, scopolamine and other known anti-cholinergic drugs do have known side-effects such as euphoria/dysphoria, memory problems, mental confusion and other CNS effects that resemble delirium. Since major depressive disorder is associated with deficits in cognitive abilities, this would produce an undesired additive effect that would only exacerbate the problem. Scopolamine is a non-selective muscarinic antagonist which is a rapidly effective antidepressant compound in humans likely mediated through an antimuscarinic effect. Unfortunately, scopolamine can produce cognitive impairment including memory disturbances in humans.

Clearly, there is a real need to identify drugs, in particular muscarinic antagonists that may be able to relieve depression without disrupting cognitive effects such as learning, memory and attention processes. In particular, there is a need to identify an improved muscarinic antagonist antidepressant wherein the antidepressant activity of the drug can be separated from cognitive impairment.

BRIEF SUMMARY OF INVENTION

The present invention relates muscarinic antagonists that function as antidepressants with cognitive impairment as a side-effect, and to methods of using these antagonists in the treatment of depression.

A first embodiment of the invention provides a method of treating depression in a subject, comprising administering a therapeutically-effective amount of one or more muscarinic antagonist to a subject in need thereof, thereby treating depression in a subject, wherein the one or more muscarinic antagonist is selected from the group consisting of CJ2100, CJ2126, CJ2162.1, CJ3007, CJ2174, L687306, CJ3018, CJ2165.1, CJ2159.3, and CJ2173.1

In certain aspects of this embodiment, the cognitive function of the subject is maintained during and after treatment. In certain other aspects of this embodiment, the one or more muscarinic antagonist is CJ2100.

A second embodiment of the invention provides a method of treating depression in a subject, comprising administering a therapeutically-effective amount of one or more muscarinic antagonist to a subject in need thereof, thereby treating depression in a subject, wherein cognitive function of the subject is maintained during and after treatment, and wherein the one or more muscarinic antagonist is selected from the group consisting of CJ2100, CJ2126, CJ2162.1, CJ3007, CJ2174, L687306, CJ3018, CJ2165.1, CJ2159.3, and CJ2173.1.

In certain aspects of this embodiment, the one or more muscarinic antagonist is CJ2100.

A third embodiment of the invention provides a method of maintaining cognitive function in a subject having depression, comprising administering a therapeutically-effective amount of one or more muscarinic antagonist to a subject in need thereof, thereby maintaining cognitive function in a subject having depression, wherein the one or more muscarinic antagonist is selected from the group consisting of CJ2100, CJ2126, CJ32162.1, CJ3007, CJ2174, L687306, CJ3018, CJ2165.1, CJ2159.3, and CJ2173.1.

In certain aspects of this embodiment, the one or more muscarinic antagonist is CJ2100.

A fourth embodiment of the invention provides a method of maintaining cognitive function and reducing depression in a subject suffering from depression, comprising administering a therapeutically-effective amount of one or more muscarinic antagonist to a subject in need thereof, thereby maintaining cognitive function and reducing depression in a subject suffering from depression, wherein the one or more muscarinic antagonist is selected from the group consisting of CJ2100, CJ2126, CJ2162.1, CJ3007, CJ2174, L687306, CJ3018, CJ2165.1, CJ2159.3, and CJ2173.1.

In certain aspects of this embodiment, the one or more muscarinic antagonist is CJ2100.

In each of the aspects and embodiments of the invention, the depression may be, but is not limited to, one or more of treatment-refractory depression, treatment-resistant depression, major depressive disorder (MDD), persistent depressive disorder, unipolar disorder, bipolar disorder, seasonal effective disorder, psychotic depression, situational depression, atypical depression, and postpartum depression.

In each of the aspects and embodiments of the invention, the therapeutically-effective amount of one or more muscarinic antagonists is may be administered to a subject in the form of a pharmaceutical composition comprising one or more muscarinic antagonists and one or more pharmaceutically acceptable diluents and/or excipients.

In each of the aspects and embodiments of the invention, the methods may be practice by further administering to the subject at least one other compound with antidepressant activity, wherein the other compound with antidepressant activity may be, but is not limited to, imipramine, amitriptyline, desipramine, nortriptlyine doxepin, protriptyline, trimipramine, maprotiline, amoxapine, trazodone, bupropion, chlomipramine, fluoxetine, duloxetine, escitalopram, citalopram, sertraline, paroxetine, flubosxamine, nefazodone, venlafaxine, milnacipran, reboxetine, lithium, mirtazapine, phenelzine, tranylcypromine, moclobemide, Kava-Kava, St. Johns Wart, s-adenosylmethionine, thyrotropin releasing hormone, neurokinin receptor antagonists, and triiodothyronine.

In each of the aspects and embodiments of the invention, the subject may be a human.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of the invention.

BRIEF DESCRIPTION OF DRAWINGS

FIG. 1 provides results from a cardiovascular assay (bradycardia test). Control animals were administered 10 mg/kg Arecoline (open circles), producing a short but pronounced bradycardia. Co-administration of 1 mg/kg CJ2100 (solid squares) attenuates this effect. CJ2100 is effective in antagonizing arecoline-induced bradycardia.

DETAILED DESCRIPTION OF THE INVENTION

I. Definitions

As used herein "a" or an may mean one or more. As used herein when used in conjunction with the word "comprising," the words "a" or "an" mean one or more than one. As used herein "another" may mean at least a second Or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. Present Invention

There are five known muscarinic receptors and all are G-protein coupled receptors (GPCRs). They differ markedly in their abundance and location within the CNS and heart. Scopolamine is an antagonist of all five muscarinic receptors that has been shown to disrupt memory and cognitive function. This effect is thought to be due to its anticholinergic properties through a muscarinic effect. There is now much effort being placed on finding compounds which while having excellent antidepressant properties, do not cause cognitive impairment in a treated subject. To date, no one has concentrated on measuring both the antidepressant and anticognitive aspects of muscarinic compounds and attempted to separate them.

Through the diligent efforts of the inventors, using a combination of synthetic chemical methods and behavioral pharmacology assays, compounds that act as muscarinic antagonists have been identified with selective properties wherein the antidepressant and anticognitive profiles can be separated and validated.

For the present invention, 3-exo-1-azabicyclo[2.2.1]heptane, 1-azabicyclo[2.2.2]octane, and N-methyltetrahydropyidine 3-substituted-1,2,4-oxadiazoles appear to be excellent scaffolds for the generation of potent muscarinic agonists/antagonists. The addition of a methyl group to the 3-position of the 1,2,4-oxadiazole yields some of the most potent muscarinic agonists currently known. Yet, addition of a cyclopropyl group appears to reduce efficacy and confer antagonist action at muscarinic sites.

Muscarinic Antagonists

From the scaffolds noted above, novel muscarinic antagonists have been developed that can be used in the treatment of depression, and the present invention is directed to these compounds and use of these compounds in the treatment of depression. When a muscarinic antagonist of the invention is administered to a subject, the subject experiences a decrease in feelings of depression. In preferred aspects of the invention, and in combination with the decrease in feelings of depression, cognitive function of the subject is maintained during and after treatment.

In particular, the invention provides the compound CJ2100, which exhibits antidepressant activity and yet does not give rise to cognitive impairment when administered to a subject. The chemical structure for CJ2100 is shown below and the chemical name of the compound is 3-(3-alkyl-1,2,4-oxadiazol-5-yl)-1,2,5,6-tetrahydro-1-methylpylidine oxalate. CJ2100 was synthesized from arecoline hydrobromide through a condensation reaction using a modified procedure of Street et al. (*J. Med. Chem.* 1990, 33(10), 2690-2697) and Showell et al. (*J. Med. Chem.*, 1991, 34, 1086-1094).

CJ2100

Other muscarinic antagonists that may be used in the methods of the invention include the following: CJ2126, CJ2162.1, CJ3007, CJ2174, L687306, CJ3018, CJ2165.1, CJ12159.3, and CJ2173.1. Thus, the muscarinic antagonists of the invention are the following compounds.

CJ2100

CJ2126

-continued

CJ2162.1

CJ3007

CJ2174

L687306

CJ3018

CJ2165.1

CJ2159.3

CJ2173.1

Methods of Treatment

The present invention is also directed to methods of treating depression in a subject via the administration of one or more of the muscarinic antagonists of the present invention, such as CJ2100, either alone or in combination with other treatments of depression.

Thus, and in one embodiment, the invention relates to a method of treating depression in a subject, comprising administering a therapeutically-effective amount of one or more muscarinic antagonist to a subject in need thereof, thereby treating depression in a subject. In preferred aspects of the method, cognitive function of the subject is maintained during and after treatment.

In another embodiment, the invention relates to a method of treating depression in a subject, comprising administering a therapeutically-effective amount of one or more muscarinic antagonist to a subject in need thereof, thereby treating depression in a subject, wherein cognitive function of the subject is maintained during and after treatment.

In another embodiment, the invention relates to a method of maintaining cognitive function in a subject having depression, comprising administering a therapeutically-effective amount of one or more muscarinic antagonist to a subject in need thereof, thereby maintaining cognitive function in a subject having depression.

In another embodiment, the invention relates to a method of maintaining cognitive inaction and reducing depression in a subject suffering from depression comprising administering a therapeutically-effective amount of one or more muscarinic antagonist to a subject in need thereof, thereby maintaining cognitive function and reducing depression in a subject suffering from depression.

In each embodiment and aspect of the methods of the invention, the muscarinic antagonist may be one or more of the following CJ2100, CJ32126, CJ2162.1, CJ3007, CJ2174, L687306, CJ3018, CJ2165.1, CJ21593, and CJ2173.1.

In particular embodiments and aspects of the methods of the invention, the muscarinic antagonist is CJ2100 as defined herein.

In each embodiment and aspect of the methods of the invention, the depression may be, but is not limited to, one or more of treatment-refractory depression, treatment-resistant depression, major depressive disorder (MDD), persistent depressive disorder, unipolar disorder, bipolar disorder, seasonal effective disorder, psychotic depression, situational depression, atypical depression, and postpartum depression.

In each embodiment and aspect of the methods of the invention, there have been no findings that airy muscarinic antagonist yields abuse liability in the subject receiving treatment.

In each embodiment and aspect of the methods of the invention, the therapeutically-effective amount of the muscarinic antagonist, such as CJ2100, administered to the subject in a discrete dose of the drug ranges from about 0.01 to about 10 mg/kg body weight of the subject. In some embodiments, the therapeutically-effective amount of the muscarinic antagonist ranges from about 0.1 to about 5 mg/kg body weight, or about 0.1 to about 3.5 mg/kg body weight, or about 0.1 to about 3.2 mg/kg body weight. Therefore, for a human subject weighing about 80 kg and in reference to this last embodiment, the treating dose of the muscarinic antagonist, such as CJ2100, may range from about 10 to about 250 mg. In other embodiments, the therapeutically-effective amount of the muscarinic antagonist ranges from about 0.1 to 1 mg/kg body weight, or from about 0.1 to 0.5 mg/kg body weight, or from about 0.1 to 0.32 mg/kg body weight.

Upon administering the therapeutically-effective amount of a muscarinic antagonist of the invention to a subject experiencing depression, the depression, or at least one symptom thereof, will be treated or reduced by at least 50, 55, 60, 65, 70, 75, 80, 85, 90, 95, 96, 97.98, 99 or 100%, versus a subject experiencing the same depression but not receiving a therapeutically-effective amount of a muscarinic is antagonist of the invention. The muscarinic antagonists of the invention can also be defined as compounds that exhibit antidepressant activity when administered to a subject, where the antidepressant activity is at least 50, 55, 60, 65, 70, 75, 80, 85, 90, 95, 96, 97, 98, 99 or 100%, versus a subject experiencing the same depression bat not receiving a therapeutically-effective amount of a muscarinic antagonist of the invention.

As used herein, the term "depression" generally means a persistent feeling of sadness and/or hopelessness, generally lasting for at least two weeks. The skilled artisan will understand that a specific definition of depression is difficult to state as the disorder can vary from person to person. However, the American Psychiatric Association provides guidelines for diagnosing depression in the Diagnostic and Statistical Manual of Mental Disorders (DSM-5), Fifth edition. 2013. Symptoms of depression can vary from mild to severe, and relevant symptoms include, but are not limited to, one or more of:

feeling sad or having a depressed mood;
loss of interest or pleasure in activities once enjoyed;
changes in appetite—weight loss or gain unrelated to dieting;
trouble sleeping or sleeping too much;
loss of energy or increased fatigue;
increase in purposeless physical activity (e.g., hand-wringing or pacing) or slowed movements and speech (actions observable by others);
feeling worthless or guilty;
withdrawal from friends/family;
difficulty thinking, concentrating or making decisions; and
thoughts of death or suicide.

Upon administering the therapeutically-effective amount of a muscarinic antagonist of the invention to a subject experiencing depression, cognitive function of the subject will be maintained at a level of at least 50, 55, 60, 65, 70, 75, 80, 85, 90, 95, 96, 97, 98, 99 or 100%, versus a subject experiencing the same depression but not receiving a therapeutically-effective amount of a muscarinic antagonist of the invention. The muscarinic antagonists of the invention can also be defined as compounds that do not give rise to cognitive impairment in a subject, where cognitive impairment is less than about 1, 2, 3, 4, 5, 10, 15, 20, 25, 30, 35, 40, 45, or 50%, versus a subject experiencing the same depression but not receiving a therapeutically-effective amount of a muscarinic antagonist of the invention.

As used herein, "cognitive function" generally refers to multiple mental abilities, including learning, thinking, reasoning, remembering, problem solving, decision making, and attention. See, e.g., Fisher et al., Chapter 2—Theories of Cognitive Aging and Work, in Work Across the Lifespan. Colorado State University, Fort Collins, CO 2019. pp 17-45.

In each embodiment and aspect of the methods of the invention, the therapeutically-effective amount of a muscarinic antagonist may be administered to a subject in the form of a pharmaceutical composition comprising one or more muscarinic antagonists and one or more pharmaceutically acceptable diluents and/or excipients.

Suitable examples of diluents and excipients are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, liospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The muscarinic antagonists and pharmaceutical compositions of the invention may be administered to a subject via suitable means that include, for example, oral, sublingual, intranasal, intraocular, rectal, transdermal, mucosal, pulmonary, topical, and parenteral routes of administration. Parenteral routes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Means for topical administration include a transdermal patch. Any known device useful for parenteral injection or infusion of drug formulations can be used to effect such administration.

Administration frequencies for the muscarinic antagonists and pharmaceutical compositions of the present invention will vary depending on the type of depression and severity of the symptoms in a particular subject. However, administration frequencies include 4, 3, 2 or once daily, every other day, every third day, every fourth day, every fifth day, every sixth day, once weekly, every eight days, every nine days, every ten days, bi-weekly, monthly and bi-monthly. The duration of time over which the muscarinic antagonists and pharmaceutical compositions are administered to a subject will be based on the type of depression being treated and will be best determined by the attending physician. However, continuation of treatment for depression is contemplated to last for a number of days, weeks, months or years. Indeed, in some instances, treatment may continue for the entire life of the subject. Depending on the means of administration, the muscarinic antagonists and compositions may be administered all at once, such as with an oral formulation in a capsule or liquid, or slowly over a period of time, such as with an intramuscular or intravenous administration.

In each embodiment and aspect of the methods of the invention, the methods may be practiced by administering one, or more than one, type of muscarinic antagonist of the invention to the subject.

In each embodiment and aspect of the methods of the invention, the methods may be practiced by administering (i) one, or more than one, type of muscarinic antagonists of the invention and (ii) at least one other compound with antidepressant activity to the subject. Suitable compounds with antidepressant activity that may be used in combination with the muscarinic antagonists of the invention include, but are not limited to, imipramine, amitriptyline, desipramine, nortriptlyine, doxepin, protriptyline, trimipramine, maprotiline, amoxapine, trazodone, bupropion, chlomipramine, fluoxetine, duloxetine, escitalopram, citalopram, sertraline, paroxetine, flubosxamine, nefazodone, venlafaxine, milnacipran, reboxetine, lithium, mirtazapine, phenelzine, tranylcypromine, moclobemide, Kava-Kava, St. Johns Wart, s-adenosylmethionine, thyrotropin releasing hormone, neurokinin receptor antagonists, and triiodothyronine.

In each of the embodiments and aspects of the invention, the subject is a human, a non-human primate, bird, horse, cow, goat, sheep, a companion animal, such as a dog, cat or rodent, or other mammal.

Methods for Identifying Muscarinic Antagonists

The present invention is also directed to methods for identifying muscarinic antagonists that exhibit antidepressant activity and yet do not give rise to cognitive impairment when administered to a subject, such as a human. An example of such muscarinic antagonists is the compound CJ2100 described herein.

It should be noted that muscarinic antagonists studied to date appear to cause a decrease in cognitive behavior while agonists enhance it. In addition, muscarinic antagonists can be effective antidepressants, muscarinic agonists are prodepressants. In order to make these assessments, drug candidates can be evaluated under the criterion that significantly smaller doses of the produced compounds will be required to produce the desired anti-depressant effects than are necessary to elicit cognitive deficits. In vivo assays can be used to initially confirm if novel compounds have antimuscarinic behavior effects in intact rats, and whether they have M2 receptor (i.e. cholinergic receptor) antagonistic activity in the peripheral nervous system (bradychardia test).

Central muscarinic effects can be elucidated by testing whether selected compounds can block the stimulus effects of arecoline and whether it can mimic the discriminative effects of scopolamine. Should the compounds be able to antagonize the bradychardia induced by arecoline, it will serve as verification of the compound as an M2 receptor antagonist (desired result). The M2 receptor is responsible for sympathetic cardiac control with agonists producing bradychardia and antagonists blocking arecoline-induced) it. The antidepressant effects will be assayed using the forced swim test (FST) primarily, with novelty-induced hypophagia (under eating) and sucrose preference test (indication of anhedonia—lack of interest in rewarding stimuli) as supportive measures. The assays have been verified and are considered reliable predictors of antidepressant action in human and rats alike.

In the FST, the rats are injected with a test compound and 30 minutes later placed individually in a cylindrical container filled with water at room temperature. The rat's behavior is videotaped from above and is later scored by a trained observed who is blind to the drug conditions. Behavior is classified every 5 seconds over the 15 minute swim period as the following: immobility the rat is hanging quietly in the water, making only enough movement to keep its nose out of the water; swimming moving limbs in an active manner, climbing or actively moving its forepaws against the side of the chamber.

In the rat sucrose preference test, rats are trained to drink a 1% sucrose solution. A baseline sucrose preference is then established prior to exposure to a chronic mild stress situation for 6 weeks in which the rats are exposed to different stressors on a daily basis. Following this exposure, sucrose preference will be re-determined in rats treated with either vehicle or muscarinic compounds. Mild stressors include 10-14 hours exposure to cat odors (kitty litter), switching from their home cage to another, rat's cage, a succession of light/dark cycles (30 minutes each), a 45 degree cage tilt, and food deprivation. Control animals have unlimited access to food/water and will be housed in a room separate from that of the stressed animals. The effect of the drug on sucrose consumption is recorded and graphed as area under the curve (AUC) using known software (PRISM). The AUC of the stressed group will be subtracted from the AUC of non-stressed to obtain a measure of the effect of the repeated stress. A measure of the effect of drug treatment will be obtained by subtracting the AUC of stressed group flour AUC of the stressed+treated group. Treatment is the between groups factor and time is the repeated measures factor.

In the novelty-induced hypophagia test, rats are trained to consume a "pleasurable" novel food (e.g., high in sugar) in their home cages for 4 days. Latency to consume and volume consumed are measured. Following these measurements rats are placed into new cages with the same food source. Latency to consume and volume are measured and compared again. Vehicle (saline), known antidepressants, and novel muscarinic compounds that have been designed are administered prior to switching the rats to their new cages. Under control treatments latency to consume increases and volume decreases (as expected) when compared to home cage environment. Antidepressants decrease latency to consume and volume consumed. This is only observed with chronic antidepressant treatment. It is expected novel compounds to be much faster acting and reverse novelty-induced hypophagia following acute treatment similar to that observed in humans.

In cognitive evaluation tests, rats are exposed to a touch screen procedure that evaluates memory (delayed matching to sample, DMTS) and attention (psychomotor vigilance). In the DTMS, a commonly used recognition task to test short-term memory, the subject (a rat) is presented with a sample stimulus. In our procedure, when the rats touch the sample stimulus it terminates on the screen. After a pre-set delay two comparison stimuli appear. A touch response on the comparison stimulus that matches some physical property of the sample stimulus (i.e. color) results in reward delivery. Touching the incorrect comparison stimulus results in a timeout. Accuracy is then plotted vs different delay values to determine a "forgetting function". This same procedure has been used by many others to assess the deleterious effects of various classes of psychoactive drugs.

Psychomotor vigilance is used to evaluate drug effects of attention and vigilance over a period of time. Championed by David Dinges of U. Penn School of Medicine, it is a reaction timed task to measure the speed with which subjects responds to a visual stimulus. In the task, stimuli of varying intensity are presented to a subject (a rat) in randomized location on the screen following unpredictable intervals. The reaction time of the rat to the stimuli will provide a reliable attention threshold in each individual subject. Attention will decrease over time which serves as a baseline for degradation of sustained vigilance. For these studies, a stimulus is presented on a screen in a random location following a variable time interval (5, 15, 30 seconds). Duration of presentation of the stimulus is 2 seconds on first trial. If the correct stimulus is touched by the rat within 2 seconds, a mild reward is delivered and duration of stimulus presentation is increased by 0.25 seconds for subsequent trials (across 500 trials).

III. Examples

Synthesis of CJ2100

CJ2100 was synthesized using the following scheme. Arecoline hydrobromide (750 mg, 3.18 mmol) was dissolved in a minimal of water (~5 mL) and a saturated solution of potassium carbonate was added (~10 mL). The solution was stirred 30 minutes at room temperature. Diethyl ether (15 mL) was added, and the layers were separated. The aqueous layer was extracted three more times with ether. The combined organic layers were dried with magnesium sulfate, filtered, and concentrated under pressure. The free base of arecoline was a light yellow oil. Desired alkylcarboxamide oxime (2.5 eq) was dissolved in dry dioxane (~15 mL) and activated 4 A sieves were added. The mixture was allowed to stir at room temperature for 30 minutes. Then sodium bromide (dry, 95%, 2.5 eq) was added in one portion and the mixture heated at 50° C. for 1 hour. Arecoline free base above was dissolved in 10 mL dioxane and activated 4 A sieves were added. The mixture was added in one portion to the solution of carboxamide and sodium hydride and heated at 90° C. overnight. The reaction was cooled to room temperature, filtered through celite, and concentrated under reduced pressure. Water was added followed by diethyl ether, and the layers were separated. Aqueous layer was extracted three more times with ether. The organic layers were combined, dried with magnesium sulfate, filtered and concentrated under reduced pressure to yield crude product. Residue was taken up into minimum amount of ethanol/ acetone, warmed to approximately 40° C., and approximately 0.85 eq oxalic acid added. The oxalate salt crystallized as the solution cooled and drops of diethyl ether were added. The pure oxalate salt was furnished in 30-60% yield.

Cardiovascular Assay (Bradycardia)

As mentioned above, muscarinic effects can be elucidated by testing whether a selected compound blocks the stimulus effects of arecoline and whether the compound can mimic the discriminative effects of scopolamine. Should a selected compound be able to antagonize the bradychardia induced by arecoline, it will serve as verification of the compound as an M2 receptor antagonist (desired result). The M2 receptor is responsible for sympathetic cardiac control with agonists producing bradychardia and antagonists blocking (arecoline-induced) it.

To measure changes in heart rate and mean arterial pressure, rats were implanted with telemetric transmitters (TA11PA-C40 or TL11M2-C50-PXT, Data Sciences International, Transoma Medical Inc., St. Paul, MN, USA) under ketamine (90 mg/kg, i.p.) and xylazine (10 mg/kg, i.p.) anesthesia. Each transmitter was placed into a subcutaneous pocket on the side of the abdomen, and the catheter extending from the base of the transmitter was inserted 2-3 cm into the femoral artery and secured with a suture. Following surgery, rats were singly-housed and allowed to recover for at least 7 days prior to experimentation. All rats continued to have free access to food and water at all times. The telemetry system consisted of battery-operated subcutaneous transmitters, Physiotel receivers, the DSI Data Exchange Matrix, and the Dataquest A.R.T. system. These transmitted, collected and stored the digital data on blood pressure and heart rate to a computer (Data Sciences International, Transoma Medical Inc., St. Paul, MN, USA). Blood pressure and heart rate data were compiled by the Dataquest A.R.T. Gold Analysis 3.01 software. At the start of an experimental session, rats in their home cages were placed on top of the receivers; heart rate data were collected for at least 1 h from undisturbed animals. Each rat was then given a saline injection to provide initial cardiovascular responses to the injection and handling procedures. Thirty min later a second injection was given, either a second saline injection or a test, compound (1 mg/kg). Fifteen min later, either saline or 10 mg/kg arecoline was given as the final injection. Data were collected for at least 2 h following the last injection. All injections were administered subcutaneously (s.c.).

The analysis program calculated an average heart rate and mean arterial pressure (MAP) every 10 s. These 10 s epochs were averaged over 1 min per rat, and data from 4 to 8 rats were averaged for each treatment group with standard error of the mean as a measure of variability with data determined for 20 min following the last injection.

Figure 1:
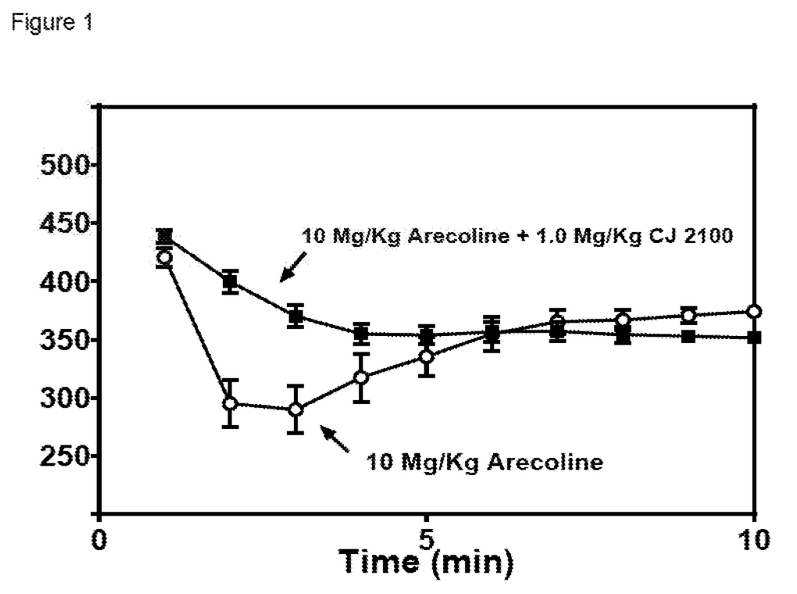

The ability of CJ2100 to antagonize arecoline-induced bradychardia was examined following this procedure. In particular, a saline solution was administered to rats as a control. Fifteen minutes later, the animals received either saline or 1 mg/kg CJ2100. This was followed by a final injection of saline or 10 mg/kg arecoline. The dose of arecoline produces a profound, but short-lived bradycardia effect. As seen from FIG. 1, the test group that also received 1 mg/kg CJ2100 showed a complete attenuation of this effect. These results demonstrate that CJ2100 is a muscarinic antagonist.

Drug Discrimination Test

The assays described in the following paragraphs are used to indicate 1) whether a test compound blocks the discriminative stimulus effects of arecoline in a surmountable fashion, and at what doses; 2) whether the test compound blocks the rate-decreasing effects of arecoline in a competitive manner, and at what doses; and 3) Whether the test compound generalizes to or antagonizes the discriminative stimulus effects of scopolamine.

Male and female Sprague-Dawley rats were trained in standard operant conditioning chambers that contain two (scopolamine vs saline or arecoline vs saline discrimination) nose-poke devices with apertures that contain yellow LED lights on either side of a dipper that can deliver 50 μl of vanilla-flavored Ensure. Rats are initially trained to nose-poke 10 times in any aperture to receive a dipper of Ensure (fixed ratio 10 FR-10 schedule of reinforcement). Nose-poke biases are noted, and the following assignments are made for the 2-nose-poke condition: 1) approximately half of the rats in each group will have the drug-associated aperture on the left, and the remaining rats will have the drug-associated aperture on the right; 2) the drug-associated aperture is assigned to the non-preferred side in half of the rats.

During training, the rats are injected with saline or their training drug and immediately placed in the chamber for a 5-min blackout, followed by a 20-min response period. If they received drug, they must respond on the drug-appropriate aperture in order to receive access to Ensure. If they received saline, they must respond on the other, saline-appropriate aperture in order to receive Ensure. Inappropriate responses result in a 1 min blackout period. Training continues until the following criteria are met: 1) responding on the first FR of the session is completed on the appropriate aperture and 2) 85% of the total responses of the session are made on the appropriate aperture.

When these criteria have been met on 3 consecutive days, testing can begin. During test sessions, the animals are injected with a dose of the test compound (or a non-training dose of the trained compound) and placed in the chambers as usual. However, during the 20-min session, 10 consecutive responses in either aperture results in delivery of Ensure. When the effects of putative antagonists are to be evaluated, these drugs are given 15 min before the start of the session, and the training drug is injected immediately before the rat is placed in the chamber. It is required that the rat meet the training criteria on two consecutive sessions between test sessions. Testing is carried out no more frequently than twice per week.

Data analysis: Full generalization to a test compound is defined as >85% responding on the drug-appropriate aperture, and completing at least one ratio. Discrimination data are expressed as the percent responses on the drug-appropriate aperture, out of the total number of responses made in both apertures. Rates of responding are calculated as well: total number of responses/time during the light-on parts of the session.

Quantitative assessment of agonist-antagonist interactions are made using individual dose-response curves and $ED_{50}$ values as determined using Graph-Pad Prism (6.0). Measurement of apparent $pA_2$ values (the dose of antagonist required to shift the agonist dose effect 2 fold to the right) or $pK_B$ values can be calculated from drug discrimination data. These values reflect the affinity of the antagonist, and when they are the same using the same antagonist in different assays, it strongly suggests that the agonist under study is acting at the same receptor in the assays (Jutkiewicz et al. (2011) Patterns of nicotinic receptor antagonism: nicotine discrimination studies. *J Pharmacol Exp Ther.* 339:194-202; Dykstra et al. (1988) Discriminative and analgesic effects of mu and kappa opioids: in vivo pA2 analysis. *Psychopharmacol Ser.* 4:107-121; Zanettini et al. (2014) Quantitative pharmacological analyses of the interaction bets flumazenil and midazolam monkeys discriminating midazolam: Determination of the functional half-life of flumazenil. *Eur J Pharmacol.* 723:405-409). To obtain these measures, Schild plots are determined by expressing the average logarithm of the dose ratio −1 as a function of the negative logarithm of the molar dose of the antagonist (Arunlakshana O. and H. O. Schild. (1959) Some quantitative uses of drug antagonists. *Br J Pharmacol* 14:48-58). Dose ratios [ratio of the $ED_{50}$ dose of the agonist in the presence of the antagonist (A') to the $ED_{50}$ dose of the agonist in the absence of the antagonist (A)] are calculated for individual rats. A straight line model of nonlinear regression is fit to the equation: log(dose ratio−1)=−log(antagonist) X slope+x-intercept at y=0.

Apparent $pA_2$ values are calculated with unconstrained slopes as well as with slopes constrained to −1. If a limited number of antagonist doses can be administered, precluding the calculation of a $pA_2$, a $pK_B$ will be calculated which is an apparent affinity estimate for a single dose of the antagonist.

Figure 2:
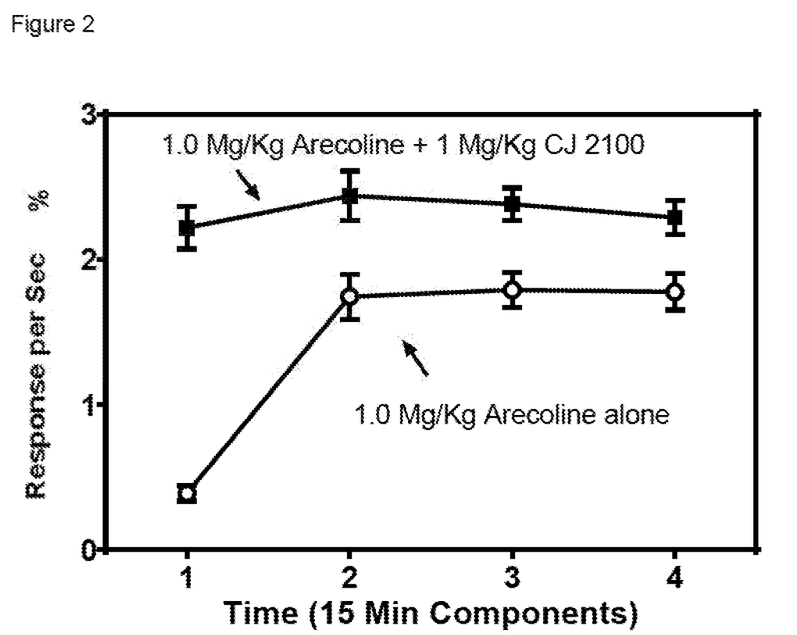
FIG. 2 shows that 1.0 mg/kg CJ2100 produced nearly 1 log unit shift to the right in the discriminative stimulus effects of arecoline (10 mg/kg; solid squares) versus control animals administered 10 mg/kg Arecoline alone (open circles).
Figure 3:
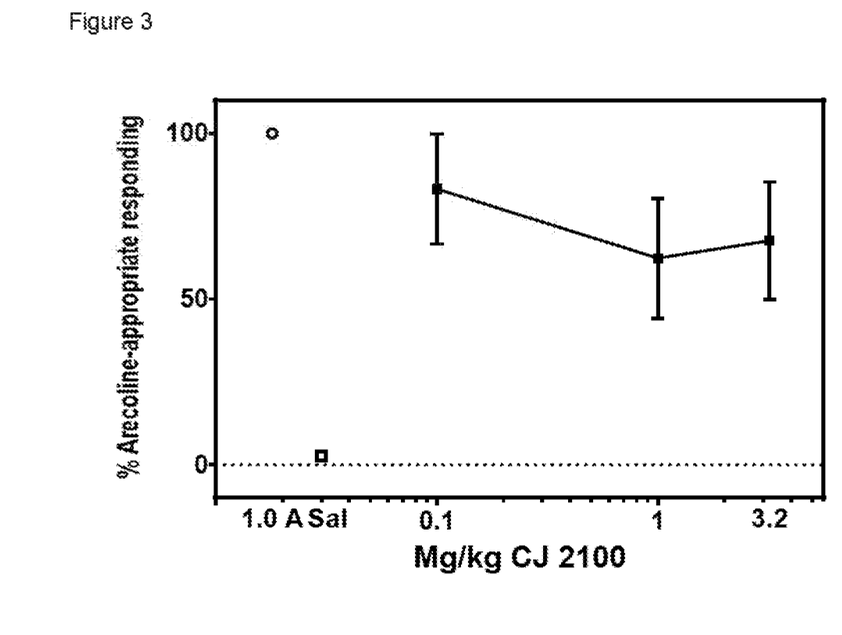
FIG. 3 shows that a similar rightward shift was produced by 1 mg/kg CJ2100 in the ability of arecoline to suppress rates of responding. Both FIGS. 2 and 3 demonstrate the antimuscarinic effect of CJ2100.

The assay was performed using CJ2100 as the test compound. The results from the assay are shown in FIGS. 2 and 3. FIG. 2 shows that 1.0 mg/kg CJ2100 produced nearly 1 log unit shift to the right in the discriminative stimulus effects of arecoline. FIG. 3 shows that a similar rightward shift was produced by 1 mg/kg CJ2100 in the ability of arecoline to suppress rates of responding.

Both FIGS. 2 and 3 demonstrate the antimuscarinic effect of CJ2100. As noted above Scopolamine was shown to be an effective antidepressant, but suffered limitations due to the cognitive deficits it produces. Scopolamine has been shown to be much less able than CJ2100 to modify either the discriminative stimulus or the rate-suppressing effects of arecoline. In fact, a dose of 1.0 mg/kg scopolamine appeared to increase the rate-modifying effects of arecoline without affecting the discriminative stimulus of arecoline (Winger et al. Comparison of the muscarinic antagonist effects of scopolamine and L-687,306. *Behav Pharmacol.* 2020 Jan. 8. Epub ahead of print), indicative of agonist-like characteristics. These results indicate that an antimuscarinic effect in the CNS (central nervous system) is likely necessary to achieve the desired pharmacological profile for a muscarinic antagonist with antidepressant potential that lacks cognitive deficits.

Forced Swim Test

Rats of both sexes as well as rats from the Flinders straw were used for forced swim tests. The rats were injected with a saline control or CJ2100 (0.1 mg/kg, 0.3 mg/kg, 1 mg/kg, or 3 mg/kg) and 30 min later placed individually a cylindrical container (46 cm tall×20 cm, diameter) filled to 30 cm with 25° C. water for a single 15-min forced swim test. Rat behavior was videotaped from above and later scored by a trained observer who was blind to the drug conditions. Behavior was classified every 5 seconds over the 15 minute swim period as following: immobility rat was hanging quietly in the water, making only enough movement to keep its nose out of the water; swimming moving limbs in an active manner, climbing, or actively moving its forepaws against the side of the chamber. A one-way ANOVA with Dunnett's post-hoc test was used when comparing more than one dose to control.

Figure 4:
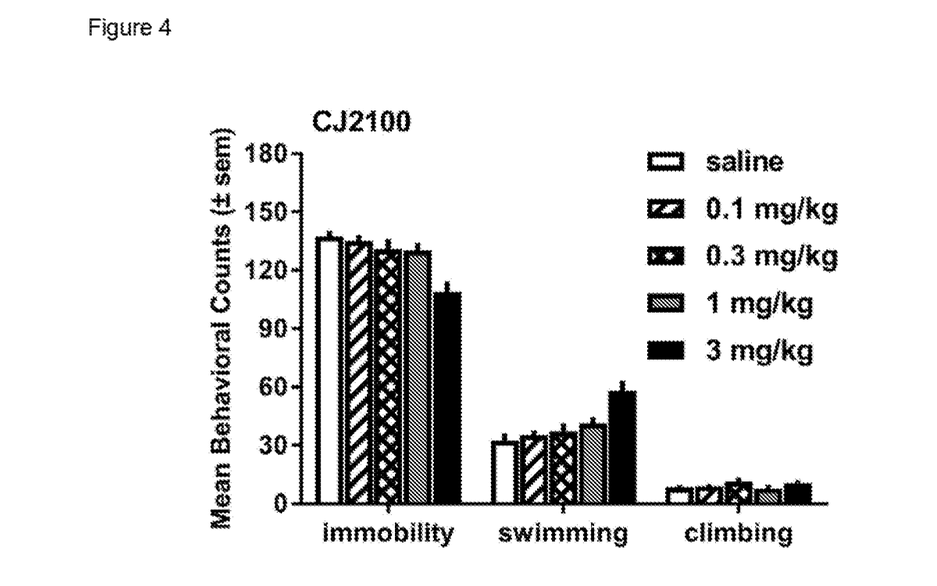
FIG. 4 provides results from forced swim tests conducted on rats receiving saline as a control or varying amounts of CJ2100 (0.1 mg/kg, 0.3 mg/kg, 1 mg/kg, 3 mg/kg). The results show the ability of 3 mg/kg to produce a decrease in immobility along with a significant increase in swimming, demonstrating the antidepressant effects of CJ2100.

The results provided in FIG. 4 demonstrate the ability of 3 mg/kg CJ 2100 to produce a decrease in immobility along with a significant increase in swimming, indicative of antidepressant-like activity associated with this muscarinic antagonist.

Cognitive Evaluation DMTS and PVT Tests

Additional tests involved a novel touch-screen procedure that evaluated memory (delayed-matching-to-sample, DMTS) and attention (psychomotor vigilance, PVT).

In the DMTS, a commonly used recognition task to test short-term memory, rats were presented with a sample stimulus. When the rats touched the sample stimulus, it terminated on the screen. After a pre-set delay, two comparison stimuli appeared. A touch response on the comparison stimulus that matched some physical property of the sample stimulus (i.e. color) resulted in reward delivery. Touching the incorrect comparison stimulus resulted in a timeout. Accuracy was then plotted vs. different delay values to determine a "forgetting function."

Psychomotor vigilance (PVT) is used to evaluate drug effects on attention and vigilance over a period of time. Championed by David Dinges of U. Penn. School of Medicine, it is a reaction-timed task to measure the speed with which subjects respond to a visual stimulus. In the task, stimuli of varying intensity were presented to the rat in randomized locations on the screen following unpredictable intervals. The reaction time of the rat to the stimuli will provide a reliable attention threshold in each individual subject. Attention decrease over time which serves as a baseline for degradation of sustained vigilance. For these studies, a stimulus was presented on a screen in a random location following a variable time interval (5, 15, 30 seconds). Duration of presentation of the stimulus was 2 seconds on first trial. If the correct stimulus was touched by the rat within 2 seconds, a milk reward was delivered and duration of stimulus presentation was increased by 0.25 seconds for subsequent trials (across 500 trials).

Figure 5:
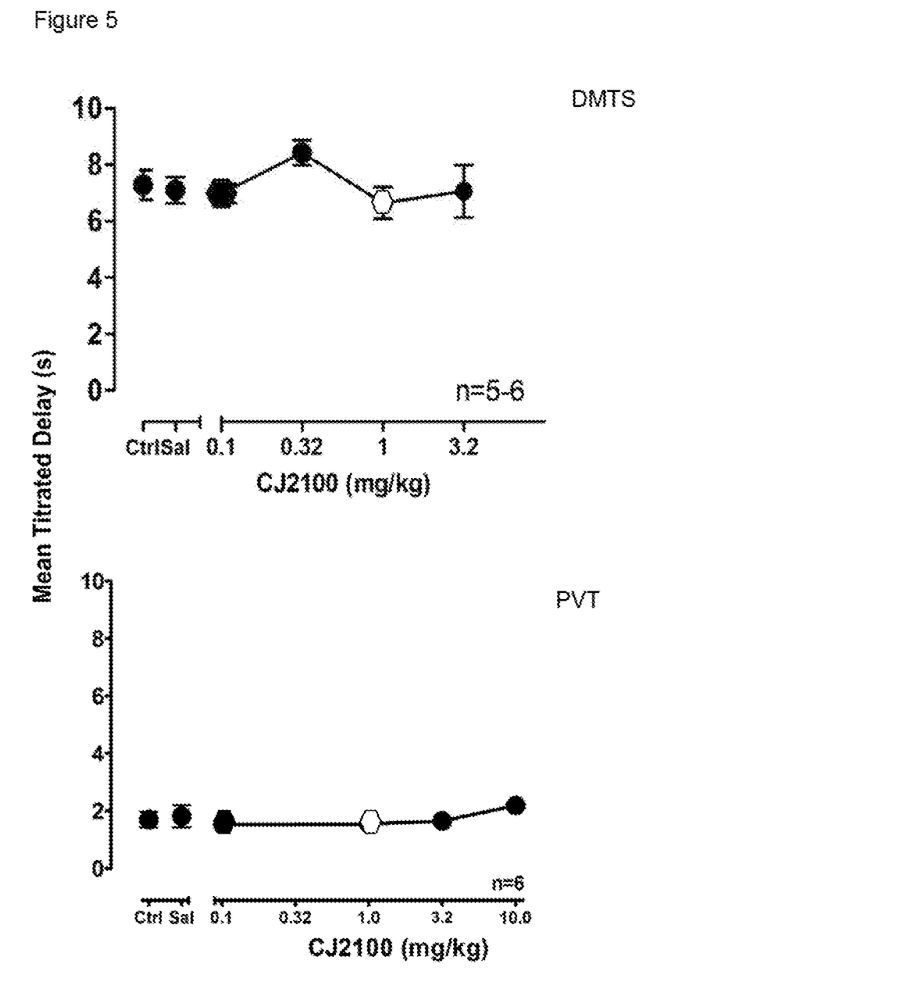
FIG. 5 provides the results from DMTS (left panel) and PVT (right panel) tasks that evaluated the Cognitive effects of CJ2100 on rats. A wide range of doses of CJ2100 (0.1-10 mg/kg, white hexagon indicates lowest effective dose in the FST) did not modify the ability of the rats to respond in this task; mean titration duration of the stimulus remained at approximately 2 sec with little variability (PVT). Similarly, a wide of doses (0.1-3.2 mg/kg) did not modify the ability of the rats to respond in the task; mean duration of short term memory remained at approximately 7 sec with little variability (DMTS).

The results provided in FIG. 5 demonstrate that a wide of doses (0.1-3.2 mg/kg) did not modify the ability of the rats to respond in the tasks; mean duration of short term memory remained at approximately 7 sec with little variability (DMTS; left panel). Additionally, a wide range of doses of CJ2100 (0.1-10 mg/kg, white hexagon indicates lowest effective dose in the FST) did not modify the ability of the rats to respond in the PVT (right panel); mean titration duration of the stimulus remained at approximately 2 sec with little variability (PVT).

As noted above, one of the limitations of scopolamine is the severe cognitive deficits it produces (effects on both attention and spatial memory). As shown in FIG. 5, CJ2100 was silent (up to 10 mg/kg in PVT and 3.2 mg/kg in DMTS) across both tasks at doses above those therapeutically effective in the FST. Therefore CJ2100 has an attractive profile as an antidepressant that lacks cognitive deficits.

While the invention has been described with reference to certain particular embodiments thereof, those skilled in the art will appreciate that various modifications may be made without departing from the spirit and scope of the invention. The scope of the appended claims is not to be limited to the specific embodiments described.

What is claimed is:

1. A method of treating depression in a subject, comprising administering a therapeutically-effective amount of one or more muscarinic antagonist to a subject in need thereof, thereby treating depression in a subject, wherein cognitive function of the subject is maintained during and after treatment, and wherein the one or more muscarinic antagonist is selected from the group consisting of CJ2100, CJ2126, CJ2162.1, CJ3007, CJ2174, L687306, CJ3018, CJ2165.1, CJ2159.3, and CJ2173.1

CJ2165.1

CJ2159.3

CJ2173.1

2. The method of claim 1, wherein the one or more muscarinic antagonist is CJ2100.

3. The method of claim 1, wherein the depression is one or more of treatment-refractory depression, treatment-resistant depression, major depressive disorder (MDD), persistent depressive disorder, unipolar disorder, bipolar disorder, seasonal effective disorder, psychotic depression, situational depression, atypical depression, and postpartum depression.

4. The method of claim 1, wherein the therapeutically-effective amount of one or more muscarinic antagonists is administered to a subject in the form of a pharmaceutical composition comprising one or more muscarinic antagonists and one or more pharmaceutically acceptable diluents and/or excipients.

5. The method of claim 1, further comprising administering to the subject at least one other compound with antidepressant activity, wherein the other compound with antidepressant activity is selected from the group consisting of imipramine, amitriptyline, desipramine, nortriptlyine, doxepin, protriptyline, trimipramine, maprotiline, amoxapine, trazodone, bupropion, chlomipramine, fluoxetine, duloxetine, escitalopram, citalopram, sertraline, paroxetine, flubosxamine, nefazodone, venlafaxine, milnacipran, reboxetine, lithium, mirtazapine, phenelzine, tranylcypromine, moclobemide, Kava-Kava, St. Johns Wart, s-adenosyl-methionine, thyrotropin releasing hormone, neurokinin receptor antagonists, and triiodothyronine.

6. The method of claim 1, wherein the subject is a human.

7. A method of maintaining cognitive function in a subject having depression, comprising administering a therapeutically-effective amount of one or more muscarinic antagonist to a subject in need thereof, thereby maintaining cognitive function in a subject having depression, wherein the one or more muscarinic antagonist is selected from the group consisting of CJ2100, CJ2126, CJ2162.1, CJ3007, CJ2174, L687306, CJ3018, CJ2165.1, CJ2159.3, and CJ2173.1

CJ2100

CJ2126

CJ2162.1

CJ3007

CJ2174

L687306

CJ3018

CJ2165.1

CJ2159.3

CJ2173.1

8. The method of claim 7, wherein the one or more muscarinic antagonist is CJ2100.

9. The method of claim 7, wherein the depression is one or more of treatment-refractory depression, treatment-resistant depression, major depressive disorder (MDD), persis- tent depressive disorder, unipolar disorder, bipolar disorder, seasonal effective disorder, psychotic depression, situational depression, atypical depression, and postpartum depression.

10. The method of claim 7, wherein the therapeutically-effective amount of one or more muscarinic antagonists is administered to a subject in the form of a pharmaceutical composition comprising one or more muscarinic antagonists and one or more pharmaceutically acceptable diluents and/or excipients.

11. The method of claim 7, further comprising administering to the subject at least one compound with antidepressant activity, wherein the other compound with antidepressant activity is selected from the group consisting of imipramine, amitriptyline, desipramine, nortriptyine, doxepin, protriptyline, trimipramine, maprotiline, amoxapine, trazodone, bupropion, chlomipramine, fluoxetine, duloxetine, escitalopram, citalopram, sertraline, paroxetine, flubosxamine, nefazodone, venlafaxine, milnacipran, reboxetine, lithium, mirtazapine, phenelzine, tranylcypromine, moclobemide, Kava-Kava, St. Johns Wart, s-adenosyl-methionine, thyrotropin releasing hormone, neurokinin receptor antagonists, and triiodothyronine.

12. The method of claim 7, wherein the subject is a human.

13. A method of maintaining cognitive function and reducing depression in a subject suffering from depression, comprising administering a therapeutically-effective amount of one or more muscarinic antagonist to a subject in need thereof, thereby maintaining cognitive function and reducing depression in a subject suffering from depression, wherein the one or more muscarinic antagonist is selected from the group consisting of CJ2100, CJ2126, CJ2162.1, CJ3007, CJ2174, L687306, CJ3018, CJ2165.1, CJ2159.3, and CJ2173.1

CJ2100

CJ2126

CJ2162.1

CJ3007

CJ2174

L687306

CJ3018

CJ2165.1

CJ2159.3

CJ2173.1

14. The method of claim 13, wherein the one or more muscarinic antagonist is CJ2100.

15. The method of claim 13, wherein the depression is one or more of treatment-refractory depression, treatment-resistant depression, major depressive disorder (MDD), persistent depressive disorder, unipolar disorder, bipolar disorder, seasonal effective disorder, psychotic depression, situational depression, atypical depression, and postpartum depression.

16. The method of claim 13, wherein the therapeutically-effective amount of one or more muscarinic antagonists is administered to a subject in the form of a pharmaceutical composition comprising one or more muscarinic antagonists and one or more pharmaceutically acceptable diluents and/or excipients.

17. The method of claim 13, further comprising administering to the subject at least one other compound with antidepressant activity, wherein the other compound with antidepressant activity is selected from the group consisting of imipramine, amitriptyline, desipramine, nortriptlyine, doxepin, protriptyline, trimipramine, maprotiline, amoxapine, trazodone, bupropion, chlomipramine, fluoxetine, duloxetine, escitalopram, citalopram, sertraline, paroxetine, flubosxamine, nefazodone, venlafaxine, milnacipran, reboxetine, lithium, mirtazapine, phenelzine, tranylcypromine, moclobemide, Kava-Kava, St. Johns Wart, s-adenosyl-methionine, thyrotropin releasing hormone, neurokinin receptor antagonists, and triiodothyronine.

18. The method of claim 13, wherein the subject is a human.

\* \* \* \* \*